United States Patent [19]

Chauthani

[11] 4,107,294

[45] Aug. 15, 1978

[54] INSECTICIDAL COMPOSITION OF *BACILLUS THURINGIENSIS* ADMIXED WITH 1-(4-CHLOROPHENYL)-3-(2,6-DIFLUOROBENZOYL)-UREA

[75] Inventor: Abdul Rehman Chauthani, Riverside, Calif.

[73] Assignee: Nutrilite Products, Inc., Buena Park, Calif.

[21] Appl. No.: 810,566

[22] Filed: Jun. 27, 1977

[51] Int. Cl.$^2$ .................... A01N 9/02; A01N 9/20; A01N 15/00
[52] U.S. Cl. ..................................... 424/93; 424/322
[58] Field of Search ........................... 424/93, 322

[56] References Cited

U.S. PATENT DOCUMENTS

| | | | |
|---|---|---|---|
| 3,086,922 | 4/1963 | Mechalas | 424/93 |
| 3,150,062 | 9/1964 | Greenberg et al. | 424/93 X |
| 3,236,622 | 2/1966 | Hartley et al. | 424/131 X |
| 3,716,634 | 2/1973 | Wells | 424/93 |
| 3,911,110 | 10/1975 | Smirnoff | 424/93 |
| 3,937,813 | 2/1976 | Clark, Jr. | 424/93 |
| 3,944,664 | 3/1976 | Kitagaki et al. | 424/93 |
| 3,946,107 | 3/1976 | Westall | 424/93 |
| 4,000,258 | 12/1976 | Shieh et al. | 424/93 |

OTHER PUBLICATIONS

Journal of Economic Entomology; vol. 67, No. 2, pp. 300–301, Neal, Jr.

Frye et al.; USDA Forest Service Research Note, Rm-315, pp. 1-7, Aug. 1976.

*Primary Examiner*—Allen J. Robinson
*Attorney, Agent, or Firm*—Burns, Doane, Swecker & Mathis

[57] ABSTRACT

An improved insecticidal composition and a method for its use are disclosed. The improved insecticidal composition comprises from 25 to 75 weight percent (by weight of the total active materials) of *Bacillus thuringiensis* and 75 to 25 weight percent (by weight of the total active materials) of 1-(4-chlorophenyl)-3-(2,6-difluorobenzoyl)-urea.

7 Claims, No Drawings

INSECTICIDAL COMPOSITION OF BACILLUS THURINGIENSIS ADMIXED WITH 1-(4-CHLOROPHENYL)-3-(2,6-DIFLUOROBENZOYL)-UREA

BACKGROUND OF THE INVENTION

*Bacillus thuringiensis*, is well-known for use as a microbial insect pathogen useful against leaf-chewing insects such as the alfalfa caterpillar, the cosmopolitan green beetle, the European corn borer and the Mediterranean flower moth. See, for example, U.S. Pat. No. 3,150,062. Although used for the toxic effects on general agricultural and forest leaf-chewing insect pests, *Bacillus thuringiensis*, has no substantial effect on sucking insects such as aphids and the like.

The search has continued for ways to increase the potency, toxicity, and/or persistance of insecticides, including *Bacillus thuringiensis*. Its use, at present, is limited to the control of early instars of the lepidoptera.

Many chemical insecticides, which are useful in controlling insects, do not control well the insect larvae belonging to the order of lepidoptera.

The search has continued for a more efficacious manner of utilizing *Bacillus thuringiensis* as a broader control insecticide. *Bacillus thuringiensis* has been suggested for use in admixture with various other insecticides, acarides or liquid carriers. See, for example, U.S. Pat. Nos. 3,946,107; 3,236,622; 3,911,110; 3,937,813; 3,944,664; and 4,000,258.

Another known insect growth regulator is 1-(4-chlorophenyl)-3(2,6-difluorobenzoyl)-urea available under the trademark "Dimilin". This compound, which is also referred to as N-4-chlorophenyl amino carbonyl-2,6-difluorobenzamide, is a chitin inhibitor effective against several economic pests, particularly foliar feeding lepidopterous insects.

OBJECTS AND SUMMARY OF THE INVENTION

It is the object of this invention to substantially avoid or alleviate the problems of the prior art.

It is further an object of this invention to provide an improved *Bacillus thuringiensis* -containing insecticide which has substantial potency.

It is also an object of this invention to provide an insecticide mixture which can control more of the stages of various lepidoptera larvae and upset the life cycle of these noxious insects.

In one aspect of the present invention, there is provided an improved insecticidal composition comprising an admixture of from about 25 to 75 weight percent by weight of total active materials of *Bacillus thuringiensis* and concomitantly from about 75 to 25 weight percent by weight of total active materials of 1-(4-chlorophenyl)-3-(2,6-difluorobenzoyl)-urea.

In another aspect of the present invention, there is provided a method for the control of areas infested with insects which comprises applying to the said insect-infested area an effective amount of the insecticidal composition of the admixtures as described above.

In still another aspect of the present invention, there is provided an improved insecticidal composition comprising the admixture of 1-(4-chlorophenyl)-3-(2,6-difluorobenzoyl)-urea with an insecticide chosen from the group consisting of *Bacillus thuringiensis* and insect viruses and a method for controlling insect-infested areas by applying theretoo this insecticidal composition.

DETAILED DESCRIPTION OF THE INVENTION

*Bacillus thuringiensis* is available in a form sufficient to be utilized as an insecticide in accordance with the present invention. It is preferred that the *Bacillus thuringiensis* be produced by the process disclosed in U.S. Pat. No. 3,086,922 herein incorporated by reference. As disclosed therein, a microbial insecticide of high spore content and potency may be produced by the steps of (a) preparing an inoculant of the *Bacillus thuringiensis* microorganism to be utilized; (b) inoculation of a nutrient medium with the prepared inoculant; (c) propagation of the inoculated medium; (d) reducing the moisture content of the propagated medium to a proper low level; (e) comminuting the dried propagated medium and metabolic products to a particle size appropriate for utilization as an insecticide.

The nutrient medium may be absorbed onto a particulate inert inorganic carrier and nutrient substrate such as volcanic glasses (e.g., perlite and the like), exfoliated vermiculite, pumice, volcanic ash, calcined diatomaceous earth and similar materials. In this manner, as fully described and exemplified in the aforesaid U.S. Pat. No. 3,086,922, the microbial insecticide may be prepared in the form of a finely divided dry particulate material having a particle size such that essentially 100 percent of the particles pass through an 80 mesh (U.S. Standard Sieve) screen. Preferably, essentially all (i.e., 99 percent or more) of the particles pass through a 100 mesh screen. The potency of the microbial insecticide is at least $15 \times 10^9$, generally at least $45 \times 10^9$, most preferably about $60 \times 10^9$, spores per gram containing approximately 3.2 percent active ingredient.

The *Bacillus thuringiensis* insecticidal material contains from about 0.5 to about 5.0 percent by weight of active *Bacillus thuringiensis*, and concomitantly from about 99.5 to about 95 percent by weight of inert materials.

1-(4-chlorophenyl)-3-(2,6-difluorobenzoyl)-urea is a potentially commercial chemical insecticide which is an insect growth regulator. The 1-(4-chlorophenyl)-3-(2,6-difluorobenzoyl)-urea is commercially available under the trademark "Dimilin" as a wettable powder with 25 percent by weight active ingredient whose particles will pass 100 percent through an 80 mesh screen.

The 1-(4-chlorophenyl)-3-(2,6-difluororbenzoyl)-urea material generally contains from about 0.5 to about 25 percent by weight of active material and concomitantly, from about 99.5 to about 75 percent by weight of inert materials.

Generally, the *Bacillus thuringiensis* is present in admixture with 1-(4-chlorophenyl-3-(2,6-difluorobenzoyl)-urea with the admixture containing from about 25 to 75, preferably 30 to 70, most preferably 35 to 70, weight percent by weight of the total active materials of *Bacillus thuringiensis* and concomitantly from about 75 to 25, preferably 70 to 30, most preferably 65 to 30, weight percent by weight of the total active materials of 1-(4-chlorophenyl)-3-(2,6-difluorobenzoyl)-urea.

The *Bacillus thuringiensis* containing particles may be blended with sufficient 1-(4-chlorophenyl)-3-(2,6-difluorobenzoyl)-urea to yield a mixture in the compositional amounts indicated above by suitable physical mixing techniques. Other suitable mixing techniques known to those skilled in the art may also be utilized.

The admixture of active materials (i.e., *Bacillus thuringiensis* and 1-(4-chlorophenyl)-3-(2,6-difluorobenzoyl)-urea and inert materials generally contains from about 0.5 to 16, preferably 1 to 14, most preferably from about 1 to 8, weight percent total active material and concomitantly from about 99.5 to 84, preferably 99 to 86, and most preferably from 99 to 92 percent by weight of the admixture of inert materials.

It has been found that the blend of *Bacillus thuringiensis* and 1-(4-chlorophenyl)-3-(2,6-difluorobenzoyl)-urea (Dimilin) not only has a more toxic effect than would be expected from the utilization of either of these materials alone but also has an improved control over the whole spectrum of larval stages of the various lepidoptera.

The improved insecticidal composition of the present invention is advantageously adapted to be packaged, handled and disseminated. In the ultimate use of the insecticidal compositions of the present invention into insect infested areas, any conventional application technique may be utilized. For example, the compositions and particularly when included with inert carrier materials are well suited for efficient and accurate application to insect infested areas from airplanes. The particles may also be dispersed in an aqueous solution and agitated and sprayed into the insect infested areas.

Although the amount of active material will vary depending upon the insect to be controlled, generally the insecticidal compositions of the present invention will be utilized in an amount of from about 0.05 to about 0.75, preferably from about 0.10 to about 0.50, most preferably from about 0.06 to about 0.10 pounds of active material per acre of treated area.

Advantageous results may also be achieved when the admixture of insecticidal materials comprises the admixture of 1-(4-chlorophenyl)-3-(2,6-difluorobenzoyl)-urea and one or more insect viruses known in the art to be effective upon lepidopterous insects. The insect viruses may be present in an amount sufficient to increase the insecticidal potency of the admixture which amount is generally in the same range as set forth above for the admixture of *Bacillus thuringiensis* and the 1-(4-chlorophenyl)-3-(2,6-difluorobenzoyl)-urea.

The invention is additionally illustrated in connection with the following Examples which are to be considered as illustrative of the present invention. It should be understood, however, that the invention is not limited to the specific details of the Examples.

EXAMPLE I

*Bacillus thuringiensis* Berliner is made in the manner of Example VI of U.S. Pat. No. 3,086,922. The prepared *Bacillus thuringiensis* material contains about 3.2 percent by weight active material on 96.8 percent by weight of growth media as an inert carrier comminuted to 100 percent minus 80 mesh and has a viable spore count of $25 \times 10^9$ spores per gram.

A portion of each of the *Bacillus thuringiensis* containing particles are admixed to form insecticidal admixtures containing the *Bacillus thuringiensis* Berliner and 1-(4-chlorophenyl)-3-(2,6-difluorobenzoyl)-urea (available under the trademark Dimilin) in admixtures having varying amounts of each of the active components.

The percent mortality rates of the individual materials and of the mixtures in tests run on cabbage looper (*Trichopulsa ni*) are shown in Table I:

TABLE I

| ACTIVE MATERIALS, WT% | | |
|---|---|---|
| *Bacillus Thuringiensis*, Berliner | 1-(4-chlorophenyl)-3-(2,6-difluorobenzoyl)-urea | Final % Mortality |
| 100 | 0 | 50 |
| 75 | 25 | 60 |
| 70 | 30 | 100 |
| 65 | 35 | 92 |
| 60 | 40 | 94 |
| 55 | 45 | 96 |
| 50 | 50 | 100 |
| 45 | 55 | 84 |
| 40 | 60 | 88 |
| 35 | 65 | 60 |
| 30 | 70 | 60 |
| 25 | 75 | 50 |
| 0 | 100 | 60 |
| 0 (Control) | 0 | 2 |

The data shows the advantageous results in final % mortality achieved with the admixtures of the present invention. The results achieved with the compositions containing from 40 to 70 weight percent of *Bacillus thuringiensis*, and 60 to 30 weight percent of 1-(4-chlorophenyl-3-(2,6-difluorobenzoyl)-urea shows a suprising and unexpected increase in final % mortality as compares with the other samples.

EXAMPLE II

The procedures and mixtures of Example I are repeated in test runs on the tobacco budworm (*Heliothis virescens*), the results of which are shown in Table II:

TABLE II

| ACTIVE MATERIALS, WT % | | |
|---|---|---|
| *Bacillus Thuringiensis*, Berliner | 1-(4-chlorophenyl)-3-(2,6-difluorobenzoyl)-urea | Final % Mortality |
| 100 | 0 | 52 |
| 75 | 25 | 46 |
| 70 | 30 | 100 |
| 65 | 35 | 100 |
| 60 | 40 | 98 |
| 55 | 45 | 98 |
| 50 | 50 | 100 |
| 45 | 55 | 88 |
| 40 | 60 | 80 |
| 35 | 65 | 80 |
| 30 | 70 | 60 |
| 25 | 75 | 50 |
| 0 | 100 | 50 |
| 0 (Control) | 0 | 0 |

This data also shows the advantageous results obtained with the admixtures of the present invention, particularly with regard to the compositions containing from 35 to 70 of the *Bacillus thuringiensis* and 65 to 30 weight percent of the 1-(4-chlorophenyl)-3-(2,6-difluorobenzoyl)-urea.

The principles, preferred embodiments, and modes of operation of the present invention have been described in the foregoing specification. The invention is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. An insecticidal composition comprising an admixture of from about 70 to 30 weight percent by weight of total active materials of *Bacillus thuringiensis*, insecticidal material and concomitantly from about 70 to 30 weight percent of total active materials of 1-(4-chlorophenyl)-3-(2,6-difluorobenzoyl)-urea.

2. The insecticidal composition of claim 1 wherein the admixture contains about 35 to 70 weight percent by weight of total active materials of *Bacillus thuringiensis,* insecticidal material and concomitantly from about 65 to 30 weight percent by weight of total active materials of 1-(4-chlorophenyl)-3-(2,6-difluorobenzoyl)-urea.

3. The insecticidal composition of claim 1 wherein the said *Bacillus thuringiensis,* active insecticidal material is contained on an inert carrier.

4. The insecticidal composition of claim 3 wherein the inert carrier is selected from the group consisting of a volcanic glass, exfoliated vermiculite, pumice, volcanic ash and calcined diatomaceous earth.

5. The insecticidal composition of claim 1 wherein the 1-(4-chlorophenyl)-3-(2,6-difluorobenzoyl)-urea is contained on an inert carrier.

6. The insecticidal composition of claim 5 wherein the *Bacillus thuringiensis,* insecticidal material contains from about 0.5 to about 5 percent by weight of active *Bacillus thuringiensis,* and concomitantly from about 99.5 to about 95 percent by weight of inert material and the 1-(4-chlorophenyl)-3-(2,6-difluorobenzoyl)-urea material contains from about 0.5 to about 25 percent by weight of active botanical material and, concomitantly, from about 99.5 to about 75 percent by weight of inert material.

7. A method for the control of areas infested with insects which comprises applying to said insect-infested area an effective amount of the insecticidal composition of claim 1.

* * * * *